(12) United States Patent
Tian et al.

(10) Patent No.: US 8,071,765 B2
(45) Date of Patent: Dec. 6, 2011

(54) PROCESS FOR THE PREPARATION OF SILDENAFIL AND INTERMEDIATES THEREOF

(75) Inventors: Guanghui Tian, Shanghai (CN); Yi Zhu, Shanghai (CN); Zheng Liu, Shanghai (CN); Zhen Wang, Shanghai (CN); Jingshan Shen, Shanghai (CN)

(73) Assignee: Topharman Shanghai Co., Ltd., Shanghai (CN)

( * ) Notice: Subject to any disclaimer, the term of this patent is extended or adjusted under 35 U.S.C. 154(b) by 249 days.

(21) Appl. No.: 12/448,425

(22) PCT Filed: Dec. 21, 2006

(86) PCT No.: PCT/CN2006/003530
§ 371 (c)(1),
(2), (4) Date: Jun. 19, 2009

(87) PCT Pub. No.: WO2008/074194
PCT Pub. Date: Jun. 26, 2008

(65) Prior Publication Data
US 2010/0048897 A1   Feb. 25, 2010

(51) Int. Cl.
C07D 487/00 (2006.01)
(52) U.S. Cl. .................................................. 544/262
(58) Field of Classification Search ............ None
See application file for complete search history.

(56) References Cited

U.S. PATENT DOCUMENTS
6,204,383 B1    3/2001   Lu et al.

FOREIGN PATENT DOCUMENTS
| CN | 1057464 | 1/1992 |
|---|---|---|
| CN | 1124926 | 6/1996 |
| CN | 1168376 | 12/1997 |

(Continued)

OTHER PUBLICATIONS

International Search Report for PCT/CN2006/003530 mailed Sep. 20, 2007.

(Continued)

*Primary Examiner* — Jeffrey Murray
(74) *Attorney, Agent, or Firm* — Nixon & Vanderhye P.C.

(57) ABSTRACT

The present invention discloses a process for preparing sildenafil and its intermediates having the structures outlined below:

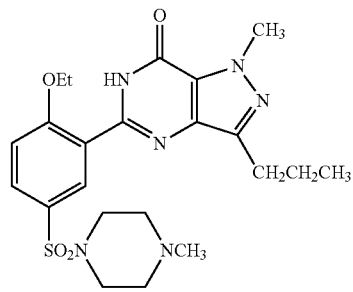

(I)

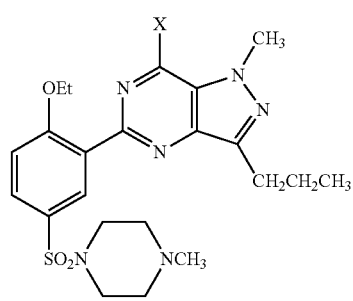

(II)

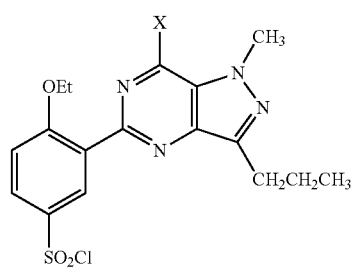

(III)

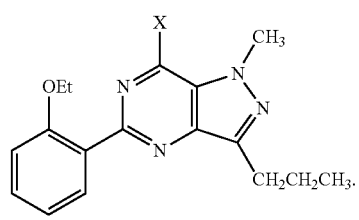

(IV)

In particular, the present invention provides a process for preparing the compound of formula (I) and its intermediates, i.e. the compounds of formula (I), (II), (III) and (IV). The compound of formula (I) is obtained from the compound of formula (II); the compound (II) is obtained from the compound of formula (III) and methylpiperazine; the compound (III) is obtained by treating the compound of formula (IV) with chlorosulfonic acid; the compound (IV) is obtained though treating the compound of formula (V) in the presence of at least one selected from $POX_3$, $PX_3$, $PX_5$ and their mixtures in any ratio. The process for preparing the compound of formula (I) according to the present invention reduces the side reactions in the processes of the prior art. These improvements lead to higher yields and a better industrial applicability with easier controlling of the reaction.

9 Claims, No Drawings

FOREIGN PATENT DOCUMENTS

| | | |
|---|---|---|
| CN | 1281851 | 1/2001 |
| CN | 1406939 | 4/2003 |
| CN | 1454892 | 11/2003 |
| EP | 0 812 845 | 12/1997 |
| WO | WO 01/19827 | 3/2001 |
| WO | WO2008074194 * | 6/2008 |
| WO | WO2008074512 * | 6/2008 |

OTHER PUBLICATIONS

Xu, Baofeng et al., Huaxue Yanjiu Yu Yingyong, Oct. 2002, 14(5): 605-607, ISSN: 1004-1656.

Khalid M. Khan, et al. A facile and improved synthesis of sildenafil (Viagra) analogs through solid support microwave irradiation possessing tyrosinase inhibitory potential, their conformational analysis and molecular dynamics simulation studies. Molecular Diversity (2005), 9(1-3): 15-26, ISSN: 1381-1991.

Baxendale et al., "Polymer-Supported Reagents for Multi-Step Organic Synthesis: Application to the Synthesis of Sildenafil", Bioorganic & Medicinal Chemistry Letters 10 (2000) 1983-1986, 4 pages.

* cited by examiner

PROCESS FOR THE PREPARATION OF SILDENAFIL AND INTERMEDIATES THEREOF

This application is the U.S. national phase of International Application No. PCT/CN2006/003530 filed 21 Dec. 2006, which designated the U.S., the entire contents of which are hereby incorporated by reference.

FIELD OF THE INVENTION

The invention relates to a process for the preparation of sildenafil and intermediates thereof.

BACKGROUND OF THE INVENTION

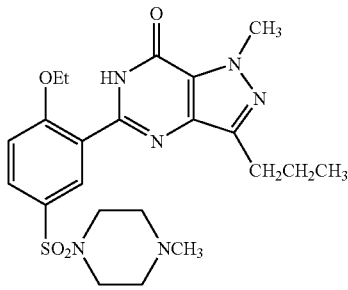

(I)

The compound of formula (I) is known as sildenafil with the chemical name of 5-[2-ethoxy-5-(4-methylpiperazin-1-ylsulphonyl)phenyl]-1-methyl-3-n-propyl-1,6-dihydro-7H-pyrazolo[4,3-d]pyrimidin-7-one. The compound was originally used in the treatment for certain cardiovascular diseases, such as angina, hypertension, heart failure, atherosclerosis and so on. Later it was found that this compound was particularly useful in the treatment for men erectile dysfunction.

Sildenafil is a selective phosphodiesterase type 5 inhibitor. This compound and its preparation method were originally disclosed in Chinese patent application CN 1,057,464A (corresponding to European patent application EP-A 463,756), and it has been found that this compound is useful in the treatment of certain cardiovascular disease. The use of sildenafil in the treatment for men erectile dysfunction was first disclosed in Chinese patent application CN 1,124,926A. An improved process for the preparation of sildenafil is described in a later application, Chinese patent application CN 1,168,376A (corresponding to EP-A 812845). CN 1,208,337C discloses a process for the preparation of sildenafil in the presence of an inorganic oxidant. Two kinds of sildenafil intermediates and processes for their preparations are described in CN 1,176,081C and CN 1,281,851A respectively. A process for the synthesis of sildenafil with a resin is also described in prior art Bioorg. Med. Chem. Lett. 2000, 10, 1983-1986. U.S. Pat. No. 6,204,383 discloses another process for the preparation of sildenafil, wherein a less basic intermediate is used and finally, a methylamine is used to close the piperazine ring to give sildenafil. In WO 2001/019827, it provides a process for the preparation of sildenafil by a methylation with formaldehyde.

Most of the processes for the preparation of sildenafil in the prior art have side-reactions, resulting in a reduced yield of the final product, which have some limitation on pharmaceutical industry.

SUMMARY OF THE INVENTION

The present invention provides a novel process for the preparation of sildenafil and intermediates thereof, which effectively overcomes the disadvantages such as some side reactions and low yields of the products in the prior art.

The technical solutions of the present invention are as follows.

The present invention provides a compound of formula (IV):

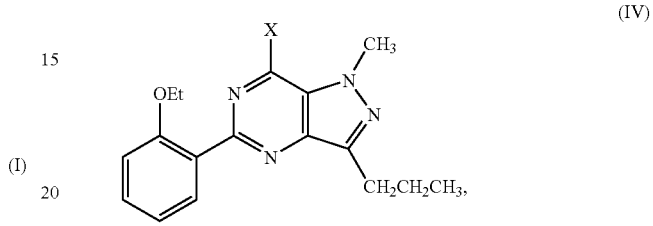

(IV)

Wherein X is Cl or Br.

The present invention further provides a process for the preparation of the compound of formula (IV), comprising the step of:

cyclizing the compound of formula (V) in the presence of at least one selected from POX$_3$, PX$_3$, PX$_5$ and their mixtures in any ratio, as illustrated in the following scheme:

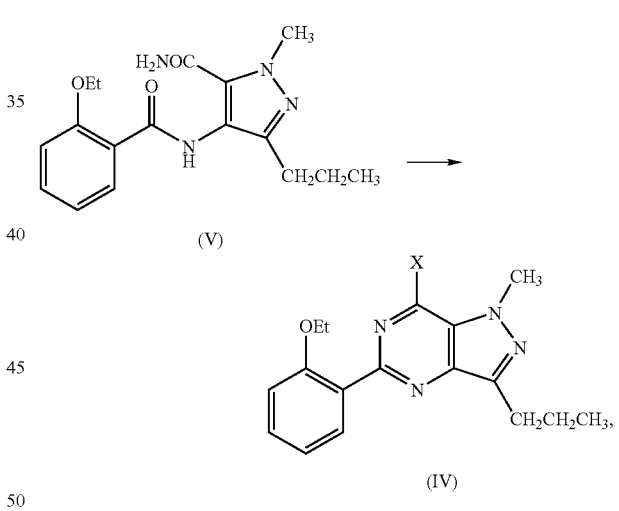

wherein X=Cl, Br; or halogenating the compound of formula (X) in the presence of at least one selected from POX$_3$, PX$_3$, PX$_5$ and their mixtures in any ratio, as illustrated in the following scheme:

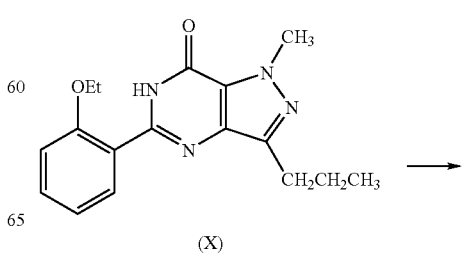

(X)

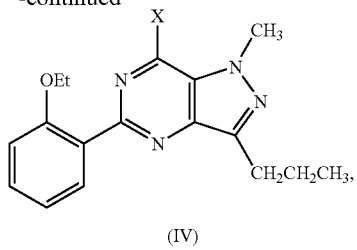

(IV)

Wherein X is Cl or Br.

In a preferred embodiment of the present invention, the process for the preparation of the compound of formula (IV) comprises one step of:

treating the compound of formula (V) in the presence of at least one selected from $POX_3$, $PX_3$, $PX_5$ and their mixtures in any ratio at 50~120° C., followed by pouring the reaction mixture into water, ice or their mixtures and collecting the precipitate which is the desired compound of formula (IV); or treating the compound of formula (X) in the presence of at least one selected from $POX_3$, $PX_3$, $PX_5$ and their mixtures in any ratio at 50~120° C., followed by pouring the reaction mixture into water, ice or their mixtures and collecting the precipitate which is the desired compound of formula (IV);

wherein X is Cl or Br.

The reaction can be carried out in the presence of a solvent selected from the group consisting of benzene, toluene, $CH_2Cl_2$, $CHCl_3$, $ClCH_2CH_2Cl$, THF, dioxane and their mixtures in any ratio.

The present invention also provides a compound of formula (III):

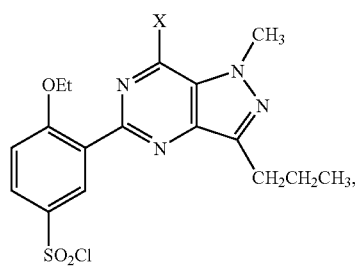

(III)

Wherein X is Cl or Br.

The present invention further provides a process for the preparation of the compound of formula (III), comprising one step of:

chlorosulfonating the compound of formula (IV) in the presence of chlorosulfonic acid, as illustrated in the following scheme:

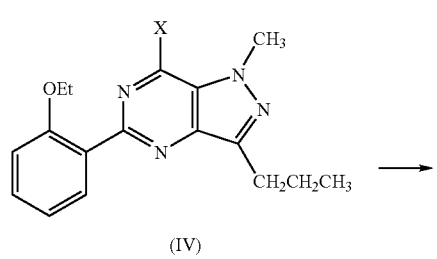

(IV)

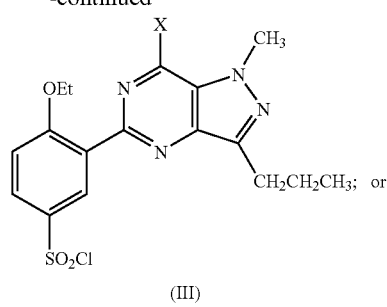

(III)

cyclizing the compound of formula (VII) in the presence of at least one selected from $POX_3$, $PX_3$, $PX_5$ and their mixtures in any ratio, as illustrated in the following scheme:

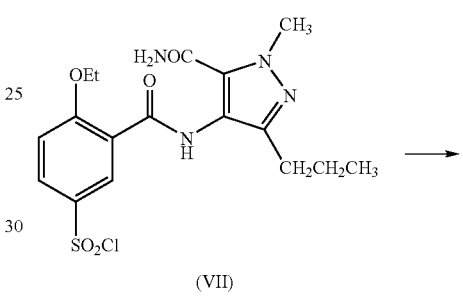

(VII)

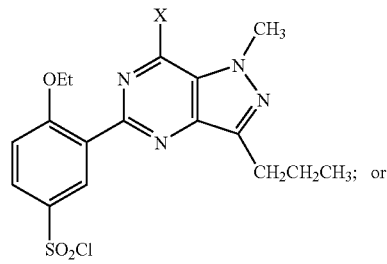

(III)

halogenating the compound of formula (VIII) in the presence of at least one selected from $POX_3$, $PX_3$, $PX_5$ and their mixtures in any ratio, as illustrated in the following scheme:

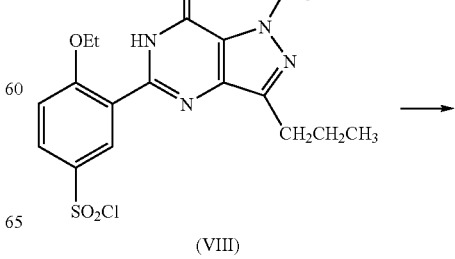

(VIII)

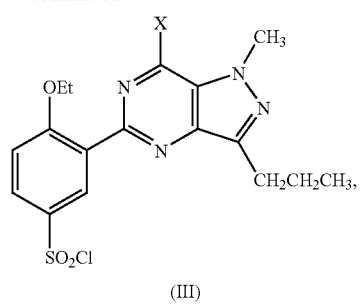

(III)

Wherein X is Cl or Br.

In another preferred embodiment of the present invention, the process for the preparation of the compound of formula (III) comprises one step of:

treating the compound of formula (IV) with chlorosulfonic acid, followed by pouring the reaction mixture into water, ice or their mixtures and collecting the precipitate to give the desired compound; or heating the compound of formula (VII) in the presence of at least one selected from $POX_3$, $PX_3$, $PX_5$ and their mixtures in any ratio at 50~120° C., followed by pouring the reaction mixture into water, ice or their mixtures and collecting the precipitate which is the desired compound of formula (IV); or heating the compound of formula (VIII) in the presence of at least one selected from $POX_3$, $PX_3$, $PX_5$ and their mixtures in any ratio at 50~120° C., followed by pouring the reaction mixture into water, ice or their mixtures and collecting the precipitate which is the desired compound of formula (IV), Wherein X is Cl or Br.

In the above process for the preparation of the compound of formula (III), the cyclization and halogenation can be carried out in the presence of a solvent selected from a group consisting of benzene, toluene, $CH_2Cl_2$, $CHCl_3$, $ClCH_2CH_2Cl$, THF, dioxane and their mixtures in any ratio.

The present invention further provides a compound of formula (II):

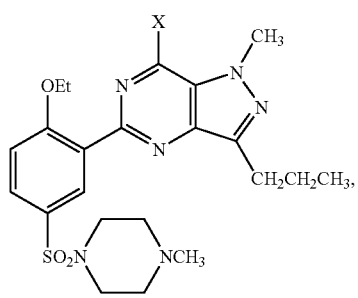

(II)

Wherein X is Cl or Br.

The present invention further provides a process for the preparation of the compound of formula (II), comprising one step of:

treating the compound of formula (III) with methylpiperazine, as illustrated in the following scheme:

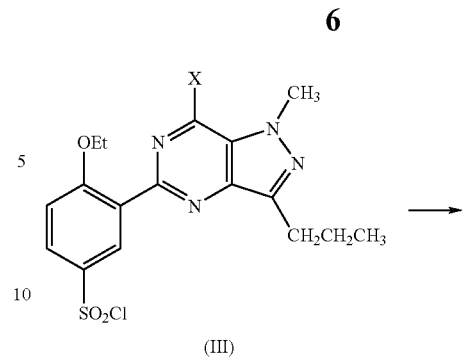

(III)

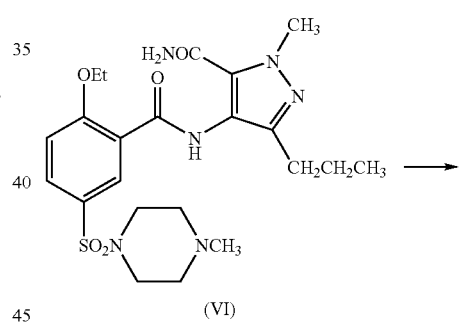

(II)

cyclizing the compound of formula (VI) in the presence of at least one selected from $POX_3$, $PX_3$, $PX_5$ and their mixtures in any ratio, as illustrated in the following scheme:

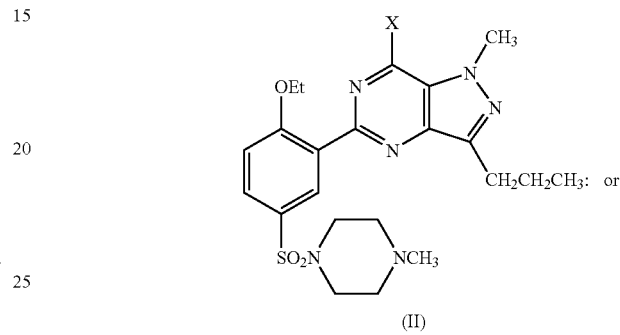

(VI)

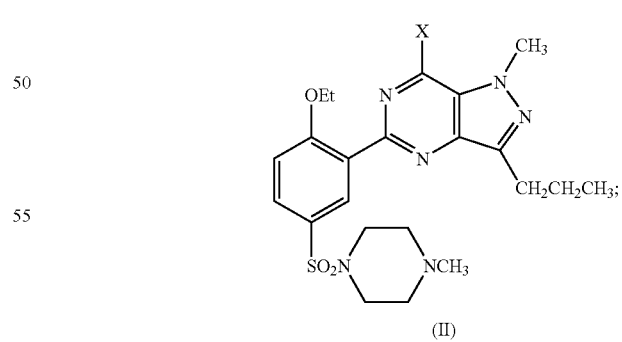

(II)

Wherein X is Cl or Br.

The compound of formula (II) can be obtained through dissolving the compound of formula (III) in a solvent selected from a group consisting of alkyl halide, lower fatty ketones and other ether solvents, followed by adding a base and methylpiperazine and collecting the desired compound from reaction mixtures; or through cyclizing the compound of formula (VI) in the presence of at least one selected from $POX_3$, $PX_3$, $PX_5$ and their mixtures in any ratio.

The cyclization mentioned above can be carried out in the presence of a solvent selected from a group consisting of benzene, toluene, $CH_2Cl_2$, $CHCl_3$, $ClCH_2CH_2Cl$, THF, dioxane and their mixtures in any ratio.

The present invention also provides a process for the preparation of the compound of formula (I), wherein the compound of formula (I) can be obtained from the compound of formula (II), as illustrated in the following scheme:

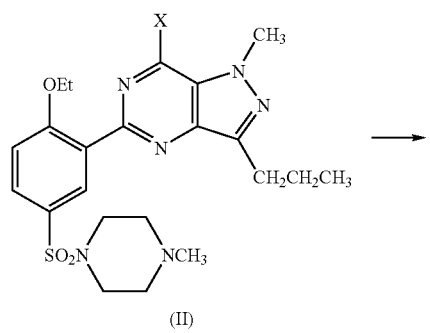

(II)

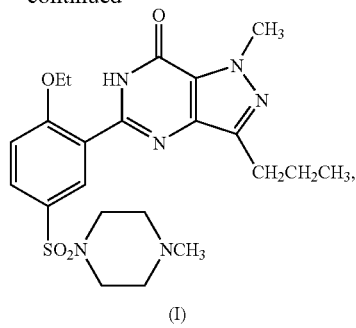

(I)

Wherein X is Cl or Br.

The above reaction can be carried out in a solvent selected from a group consisting of water, methanol, ethanol, isopropanol, t-$C_4H_9OH$, glycol, ethylene glycol monomethyl ether and mixtures thereof. Furthermore, it can be optionally carried out by further adding a base selected from a group consisting of alkali metal alkoxides, alkali metals, alkaline earth metal hydrides, organic bases such as an organic amine, amine metal derivatives, hydroxides, carbonates, bicarbonates and their mixtures in any ratio, or adding an acid selected from a group consisting of hydrochloric acid, sulfuric acid, phosphoric acid, organic acids such as citric acid, tartaric acid, maleic acid and mixtures thereof in any ratio.

In the process for the preparation method of the compound of formula (I), the intermediate (II) can be obtained through above process.

Specifically, the process for the preparation of compound (I) according to the present invention is outlined in scheme 1:

Scheme 1

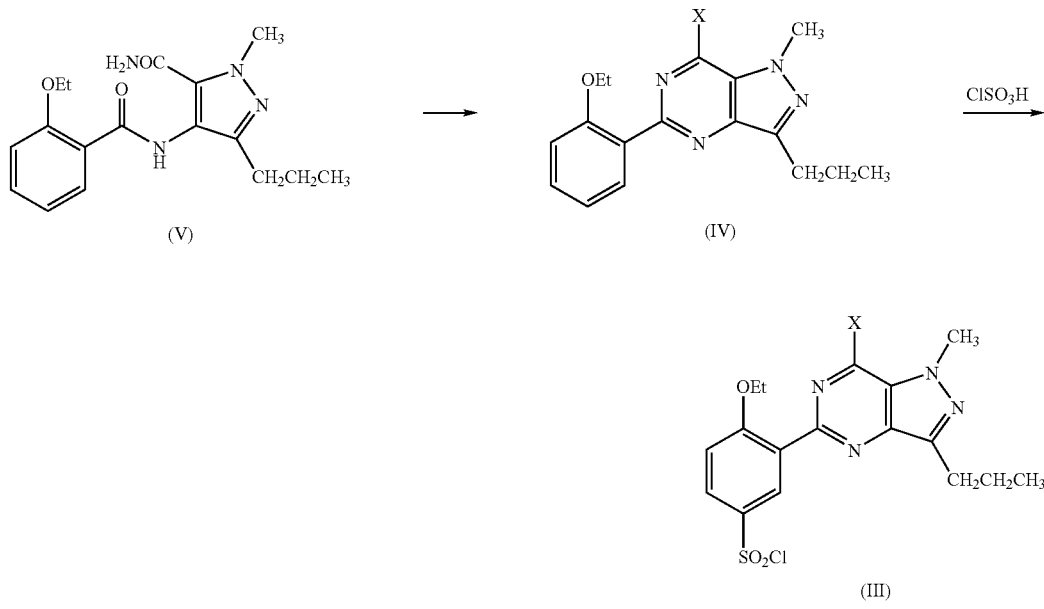

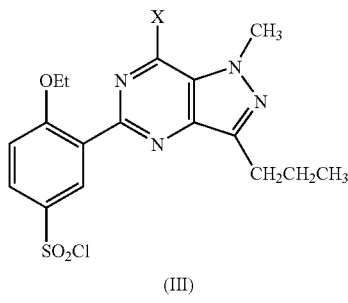

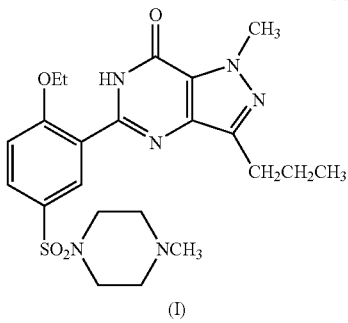

(I)

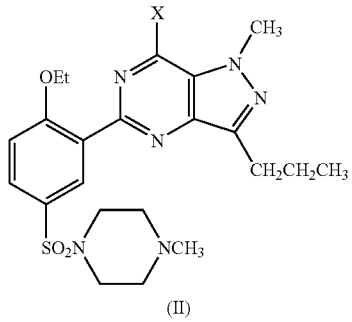

(II)

Wherein X is Cl or Br.

The present invention reduces the side reactions in base cyclization and other steps in the preparation of sildenafil as compared with the processes in the prior art, resulting in higher yields, more convenient operation, and thus better industrial applicability.

DETAILED DESCRIPTION OF THE INVENTION

Hereinafter, the processes for the preparation of the compounds of formula (I), (II), (III) and (IV) according to the present invention will be described in detail in combination with the following examples.

In the following examples, X is Cl or Br.

Starting from the compound of formula (V), the compound of formula (III) can be obtained from the intermediate of formula (IV) or synthesized by one-pot synthesis. The latter method is that the compound of formula (V) is cyclized followed by adding chlorosulfonating reagent without purification. The detailed procedure is as follows.

The compound of formula (IV) is added into $POX_3$ or $PX_3$ in an ice bath. After 10 minutes, the mixtures is heated slowly to 80° C. for 1~10 hours. When the reaction is finished, the mixture is cooled to room temperature and chlorosulfonic acid is added slowly in an ice bath. After stirred at room temperature for 1~5 hours, and the mixture is poured into water, crash-ice or their mixtures. The precipitated white solid is filtered off and washed with ice-water, followed by being dried under vacuum to obtain the compound of formula (III).

This reaction can be carried out in an appropriate solvent selected from a group consisting of benzene, toluene, $CH_2Cl_2$, $CHCl_3$, $ClCH_2CH_2Cl$, THF, dioxane and mixtures thereof.

In the reported processes for the preparation of sildenafil, the cyclization is carried out in the presence of a strong base, which usually results in many side reactions, e.g. the isomerization of pyrimidine skeleton and cleavage of the 5-ethoxy group on benzene ring. Therefore, the yield is low. The present invention overcomes the disadvantages of the conventional processes. The cyclization is carried out in the presence of $POX_3$ or $PX_3$, to give a stable cyclized product without side reactions of isomerization of pyrimidine skeleton and cleavage of the ethoxy group on benzene ring. Furthermore, in the subsequent step of chlorosulfonation, the remained $POX_3$ can prevent the hydrolysis of the compound of formula (III). Accordingly, the yield is increased greatly.

The compound of formula (II) is obtained by treating the compound of formula (III) with 1-methylpiperazine in the presence of a de-acid reagent. In detail, the compound of formula (III) is dissolved in an appropriate solvent, followed by the addition of a de-acid reagent. The reaction temperature is kept under 10° C. and about 1.1 equivalent of 1-methylpiperazine is added slowly. After stirred for 1~3 hours at room temperature, distilled water is added and the mixture is extract with an organic solvent. The organic phase is washed by saturated $NH_4Cl$ and brine, dried over $Na_2SO_4$, and evaporated under vacuum to give the desired compound of formula (II) as a white powder.

The appropriate solvent can be selected from a group consisting of alkyl halides such as $CH_2Cl_2$, $CHCl_3$, $ClCH_2CH_2Cl$, lower fatty ketones such as acetone, and ethers such as THF and ethylene glycol monomethyl ether.

The de-acid reagent can be selected from a group consisting of inorganic bases such as carbonate, bicarbonate, hydroxide, and organic bases such as triethylamine.

The process for preparing sildenafil from the compound of formula (II) can be carried out under base, neutral or acidic conditions. The base is selected from a group consisting of alkali metal alkoxides, alkali metal hydrides, alkaline earth metal hydrides, amines (triethylamine is preferred), amine metal derivatives, hydroxides, carbonates, bicarbonates and their mixtures. The acid is selected from a group consisting of hydrochloric acid, sulfuric acid, phosphoric acid, organic acids such as citric acid, tartaric acid and maleic acid, or mixtures thereof. The solvent is selected from a group consisting of water, and mixtures of water with methanol, ethanol, isopropanol, t-$C_4H_9OH$, glycol, ethylene glycol monomethyl ether. For example, the compound of formula (II) is dissolved in a mixed solvent of water and tert-butanol, followed by the addition of a molar equivalent of $NaHCO_3$. The mixture is heated at 70° C. for 2 hours to give the compound of formula (I).

The compound of formula (III) can be obtained from cyclization of the compound of formula (VII) or halogenation of the compound of formula (VIII), as illustrated in the following schemes,

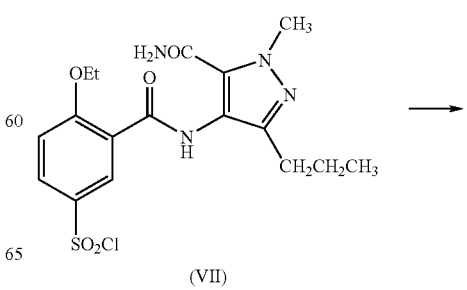

(VII)

-continued

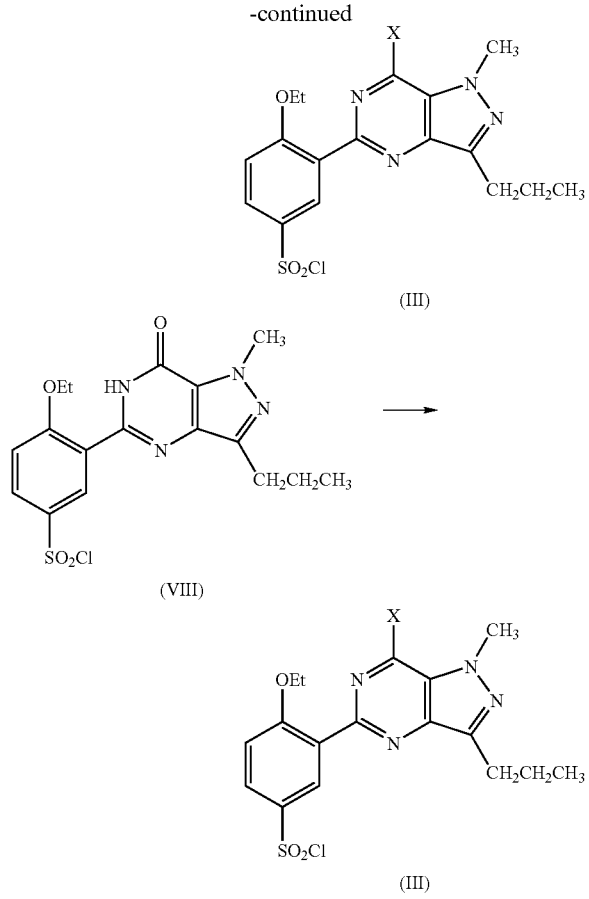

Wherein X is Cl or Br.

The compound of formula (IV) can be obtained from halogenation of the compound of formula (X)

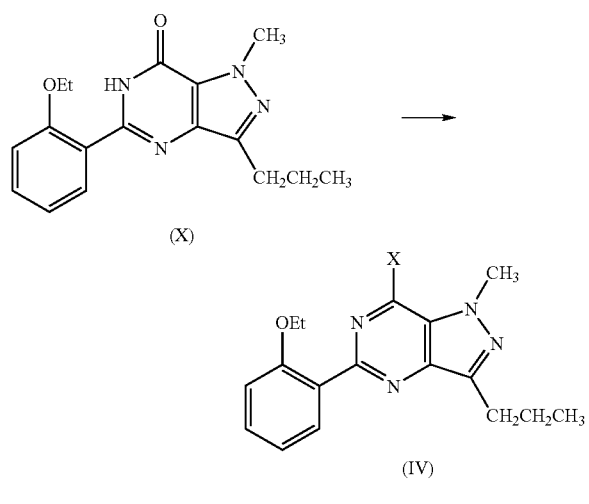

Wherein X is Cl or Br.

The three reactions mentioned above can be carried out in the presence of at least one selected from $POX_3$, $PX_3$, $PX_5$ and mixtures thereof. Alternatively, they can be performed in solvents such as benzene, toluene, $CH_2Cl_2$, $CHCl_3$, $ClCH_2CH_2Cl$ or other solvents.

The compound of formula (II) can be obtained from the compound of formula (VI) in the presence of $POCl_3$, as illustrated in the following scheme,

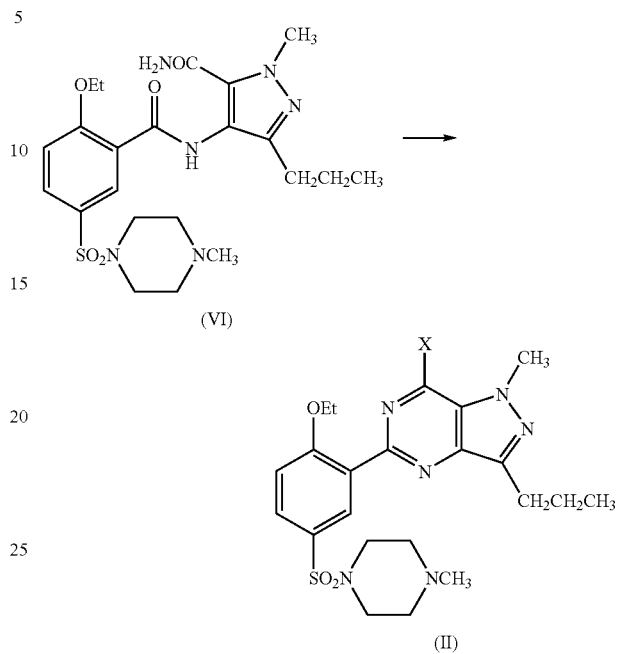

Wherein X is Cl.

The preparation of the compound of formula (VIII) and (X) used in the process according to the present invention can be refer to prior art CN 1,028,758C.

The preparation of the compound of formula (VI) used in the process according to the present invention can be refer to prior art CN 1,106,399C.

The intermediate (V) used in the process according to the present invention can be prepared by a conventional process known in the literature. For example, it can be obtained through treating 2-ethoxybenzoyl chloride with 1-methyl-3-propyl-4-aminopyrazole-5-carboxamide, as illustrated in the following scheme.

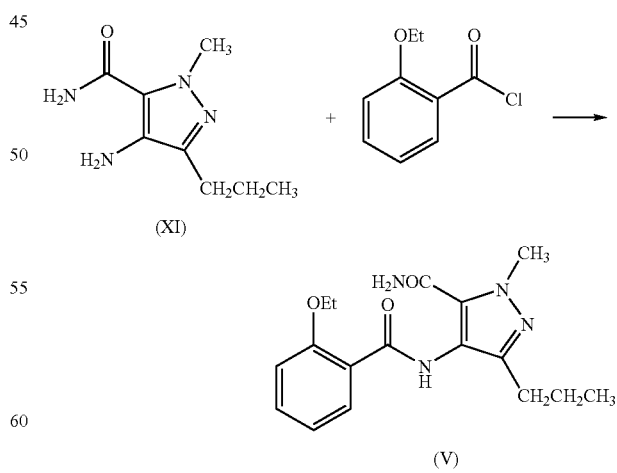

The compound of formula (VII) can be obtained from the compound of formula (V) by a conventional process known in the literature, for example, as illustrated in the following scheme.

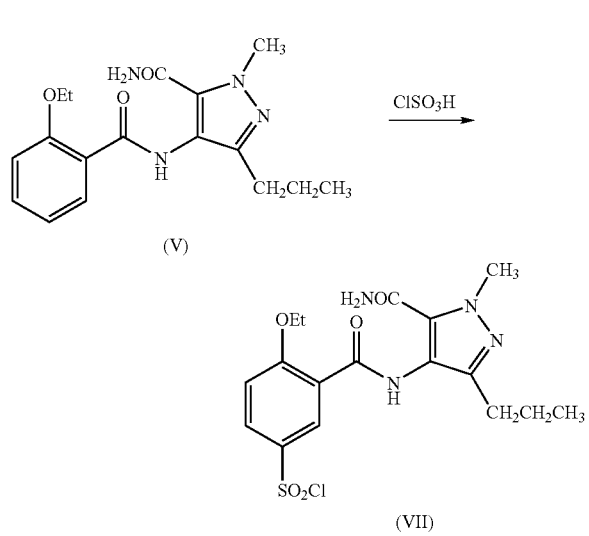

The process according to present invention reduces side reactions in the previous processes, e.g. the isomerization of pyrimidine skeleton and cleavage of the 5-ethoxy group on benzene ring in alkali-catalyzed cyclization. These improvements lead to higher yields and easier controlling of the reaction, resulting in a better industrial applicability.

The following examples serve to explain the present invention, but are not intended to limit the scope of the invention. All of the above technical solutions of the present invention can realize the object of the invention.

EXAMPLES

All the solvents or reagents used in the experiments were commercial available from Sinopharm Chemical Reagent Co., Ltd. Melting points were measured in open capillaries on a BUCHI-510 melting point apparatus without correction. MS spectra were measured on a Finnigan MAT-95 spectrometer at 70 eV. $^1$H NMR spectra were determined in CDCl$_3$ solution on a Varian Mercury 300 spectrometer. All the spectrum results were agreed well with the expected results. Conventional abbreviations were used for designation of major peaks: e.g. s, singlet; d, doublet; t, triplet; q, quartet; m, multiplet. Room temperature used herein means a temperature in the range of from 20 to 25° C.

Example 1

Preparation 1

1-methyl-3-n-propyl-4-(2-ethoxybenzamido)-pyrazole-5-carboxamide (V)

To a 250 mL three-neck flask, were added the compound of formula (XI) (20 g, 0.11 mol), dichloromethane (100 mL) and triethylamine (22.2 g, 0.22 mol) to prepare a solution in an ice bath below 5° C., followed by the slow addition of 2-ethoxybenzoyl chloride. After the mixture was stirred at room temperature for 2 hours, water (40 mL) was added to quench the reaction, and the layers were separated. The organic phase was washed with brine (30 mL) and saturated aqueous sodium hydrogen carbonate solution, dried over anhydrous sodium sulfate, followed by concentration. The resulting residue was purified by re-crystallising with ethyl acetate/petroleum ether to obtain the compound of formula (V) (31.5 g, yield 87%) as a white solid. m.p. 153~154° C.; $^1$H NMR (CDCl$_3$, 300 MHz) δ: 0.93 (3H, t), 1.54 (3H, t), 1.65 (2H, m), 2.54 (2H, t), 4.06 (3H, s), 4.31 (2H, q), 5.62 (1H, br s), 7.05 (1H, d), 7.13 (1H, t), 7.54 (1H, t), 7.91 (1H, br s), 8.27 (1H, dd), 9.47 (1H, s).

Preparation 2

4-[2-ethoxy-5-chlorosulphonyl-benzamido]-1-methyl-3-n-propyl-pyrazole-5-carboxamide (VII, X=Cl)

In a 25 mL flask, the compound of formula (V) (5 g, 0.015 mol) was added slowly to chlorosulfonic acid (10 mL) in an ice bath. After the mixture was stirred in the ice bath for 30 minutes, the ice bath was removed and the reaction continued for another 2 hours. Then the reaction mixture was poured into 20 mL of ice-water. The resulting white solid was collected by filtration, washed with ice-water until the filtrate was neutral, dried under vacuum to obtain the compound of formula (VII) (3.5 g) as a white solid in a 54% yield. $^1$H NMR (CDCl$_3$, 300 MHz) δ: 0.94 (3H, t), 1.62 (3H, t), 1.66 (2H, m), 2.53 (2H, t), 4.06 (3H, s), 4.46 (2H, q), 5.72 (1H, s), 7.25 (1H, t), 7.62 (1H, s), 8.18 (1H, dd), 8.95 (1H, d), 9.20 (1H, s).

Preparation 3

7-chloro-1-methyl-5-(2-ethoxyphenyl)-3-n-propyl-1,6-dihydro-7H-pyrazolo[4,3-d]pyrimidine (IV, X=Cl)

Method 1

The compound of formula (V) (5 g, 0.015 mol) from Preparation 1 was added into a 50 mL three-neck flask in an ice bath. POCl$_3$ (20 mL) was added dropwise into the flask to prepare a solution. After heated at 80° C. for 2 hours, the mixture was poured into 20 mL of ice-water to quench the reaction, and extracted with dichloromethane (3×30 mL). The combined organic phase was washed with brine (2×10 mL) and dried over anhydrous sodium sulfate (2 g), followed by concentration in vacuo to give the compound of formula (IV) (4.1 g, yield 82%) as a white solid. $^1$H NMR (CDCl$_3$, 300 MHz) δ: 1.03 (3H, t), 1.38 (3H, t), 1.90 (2H, m), 3.10 (2H, t), 4.15 (2H, q), 4.38 (3H, s), 7.03 (1H, d), 7.07 (1H, t), 7.42 (1H, t), 7.79 (1H, dd); EI-MS m/z 330 (M$^+$, 76), 332 (25), 315 (52), 317 (15), 294 (100), 296 (32), 279 (60), 261 (28), 159 (20).

Method 2

The compound of formula (X) (5 g, 0.015 mol) was added into a 50 mL three-neck flask in an ice bath. POCl$_3$ (20 mL) was added dropwise into the flask to prepare a solution. After heated at 80° C. for 2 hours, the mixture was poured into 20 mL of ice-water to quench the reaction, and extracted with dichloromethane (3×30 mL). The combined organic phase was washed with brine (2×10 mL) and dried over anhydrous sodium sulfate (2 g), followed by concentration in vacuo to give the compound of formula (IV) (4.4 g, yield 83%) as a white solid.

Method 3

In a 50 mL three-neck flask, the compound of formula (V) (5 g, 0.015 mol) from Preparation 1 was dissolved in benzene (20 mL), followed by dropwise addition of a solution of POCl$_3$ (2.8 mL) in benzene (5 mL) in an ice bath. After the ice bath was removed, the reaction mixture was heated at 80° C. for 3 hours, and then the benzene was removed by distillation under reduced pressure. The residue was poured into ice-water (20 mL) and the solution was extracted with dichloromethane (3×30 mL). The combined organic phase was washed with brine (2×10 mL) and dried over anhydrous sodium sulfate (2 g), followed by concentration to give the compound of formula (IV) (3.6 g, yield 72%) as a white solid.

Preparation 4

7-chloro-1-methyl-5-(2-ethoxy-5-chlorosulfonylphenyl)-3-n-propyl-1,6-dihydro-7H-pyrazolo[4,3-d]pyrimidine (III, X=Cl)

Method 1

The compound of formula (V) (5 g, 0.015 mol) from Preparation 1 was added into a 50 mL three-neck flask in an ice bath, and then $POCl_3$ (10 mL) was added dropwise. The reaction mixture was heated at 80° C. for 2 hours, and then cooled to a temperature below 5° C. Chlorosulfonic acid (10 mL) was added into the reaction mixture. 30 minutes later, the ice bath was removed, and the reaction mixture was stirred at the room temperature for 2 hours. The mixture was poured into ice-water (20 mL). The resulting solid was collected by filtration, washed with ice-water until the filtrate was neutral, dried under vacuum for 3 hours to obtain the compound of formula (III) (5.7 g) in a 88% yield, m.p. 155~156° C.; $^1$H NMR (CDCl$_3$, 300 MHz) δ: 1.04 (3H, t), 1.43 (3H, t), 1.89 (2H, m), 3.09 (2H, t), 4.27 (2H, q), 4.42 (3H, s), 7.19 (1H, d), 8.10 (1H, dd), 8.46 (1H, d); EI-MS m/z 430 (31), 428 (M$^+$, 41), 413 (45), 415 (34), 393 (20), 357 (24), 328 (25), 292 (100).

Method 2

The compound of formula (IV) (3 g) from Preparation 2 was added into a 50 mL flask and then chlorosulfonic acid (6 mL) was added to prepare a solution in an ice bath. 30 minutes later, the ice bath was removed. After stirred at room temperature for 2 hours, the mixture was poured into ice-water (15 mL), the resulting white solid was collected by filtration, washed with ice-water until the dropwise filtrate was neutral, and dried under vacuum at 35° C. for 3 hours to obtain the compound of formula (III) (2.8 g, yield 72%).

Method 3

The compound of formula (VII) (5 g, 0.012 mol) was added into a 50 mL flask, and $POCl_3$ (10 mL) was added slowly to prepare a solution. After heated at 80° C. for 2 hours, the reaction mixture was poured into ice-water (20 mL). The resulting white solid was collected by filtration, washed with ice-water until the dropwise filtrate was neutral, and dried in vacuo to obtain the compound of formula (III) (3.2 g, yield 64%).

Method 4

The compound of formula (VIII) (5 g, 0.012 mol) was added into a 50 mL flask, and $POCl_3$ (10 mL) was added slowly to prepare a solution. After heated at 80° C. for 2 hours, the reaction mixture was then poured into ice-water (20 mL). The resulting white solid was collected by filtration, washed with ice-water until the dropwise filtrate was neutral, and dried under vacuum to obtain the compound of formula (III) (4.8 g, yield 92%) as a white solid.

Method 5

The compound of formula (VIII) (5 g, 0.012 mol) was added into a 50 mL flask, and $POC_3$ (10 mL) was added slowly to prepare a solution. After heated at 70° C. for 2 hours, the reaction mixture was then poured into ice-water (20 mL). The resulting white solid was collected by filtration, washed with ice-water until the dropwise filtrate was neutral, and dried in vacuo to obtain the compound of formula (III) (4.0 g, yield 77%) as a white solid.

Method 6

In a 50 mL flask, the compound of formula (VIII) (5 g, 0.012 mol) was dissolved in benzene (40 mL), and $PCl_5$ (3.8 g) was added into the solution in an ice bath. 30 minutes later, the ice bath was removed, and the reaction mixture was heated at 90° C. for 2 hours and then poured into ice-water (20 mL). The resulting solid was collected by filtration, washed with ice-water until the dropwise filtrate was neutral, and dried in vacuo to obtain the compound of formula (III) (3.5 g, yield 67%) as a white solid.

Preparation 5

7-chloro-1-methyl-5-[2-ethoxy-5-(4-methylpiperazinylsulphonyl)phenyl]-3-n-propyl-1,6-dihydro-7H-pyrazolo[4,3-d]pyrimidine (II, X=Cl)

Method 1

In a 50 mL flask, the compound of formula (III) (2 g) from Preparation 2 was dissolved in dichloromethane (20 mL), followed by addition of triethylamine (0.94 g, 9.3 mmol) to prepare a solution. A solution of 1-methylpiperazine (0.51 g, 5.1 mmol) in dichloromethane (5 mL) was then added dropwise to the solution in an ice bath. After the ice bath was removed, the mixture was stirred at room temperature for 2 hours. 10 mL of water was added, and the layers were separated. The organic phase was washed with saturated aqueous ammonium chloride solution (2×5 ml) and brine (2×5 mL), and dried over anhydrous $Na_2SO_4$ (1 g) for 30 minutes. The solvent was removed by distillation under reduced pressure to afford crude of formula (II) as a white solid, which was the purified by re-crystallising with dichloromethane/petroleum ether to obtain a white needle crystal (1.95 g, yield 85%). m.p. 157~159° C.; $^1$H NMR (CDCl$_3$, 300 MHz) δ: 1.03 (3H, t), 1.41 (3H, t), 1.90 (2H, m), 2.41 (3H, s), 2.69 (4H, s), 3.04 (2H, t), 3.23 (4H, s), 4.19 (2H, q), 4.37 (3H, s), 7.10 (1H, d), 7.78 (1H, dd), 8.17 (1H, s); EI-MS m/z 494 (2), 492 (M$^+$, 6), 424 (2), 422 (7), 330 (7), 99 (100).

Method 2

The compound of formula (VI) (2 g, 0.004 mol) was added into a 50 mL flask, and $POCl_3$ (10 mL) was added slowly to prepare a solution. After heated at 80° C. for 2 hours, the reaction mixture was then poured into ice-water (8 mL). The resulting white solid was collected by filtration, washed with ice-water until the dropwise filtrate was neutral, and dried under vacuum to obtain a white solid (1.5 g, yield 75%).

Method 3

In a 50 mL flask, the compound of formula (VI) (2 g, 4 mmol) was dissolved in benzene (10 mL), and a solution of $POCl_3$ (0.65 mL) in benzene (2 mL) was added slowly to the solution. The reaction mixture was heated at 80° C. for 2 hours and then poured into ice-water (8 mL). The resulting white solid was collected by filtration, washed with ice-water until the dropwise filtrate was neutral, and dried under vacuum to obtain a white solid (1.4 g, yield 70%).

Preparation 6

1-methyl-5-[2-ethoxy-5-(4-methylpiperazin 1-ylsulphonyl)phenyl]-3-n-propyl-1,6-dihydro-7H-pyrazolo[4,3-d]pyrimidin-7-one (1)

Method 1

In a 25 mL flask, the compound (II) (1 g) from Preparation 4 was dissolved in tert-butyl alcohol (3 mL) and water (3 mL) to prepare a solution, followed by addition of $NaHCO_3$ (0.17 g, 2.1 mmol). After the mixture was heated to reflux for 2 hours, the tert-butyl alcohol was removed by distillation under reduced pressure. The PH value of the reaction mixture was adjusted to 8.5~9.5 with 1 mol/L HCl aqueous solution in an ice-water bath. The resulting white solid was collected by filtration, and purified by re-crystallising with ethanol to obtain a white needle crystal (0.87 g, yield 90%). m.p.

186~188° C.; $^1$H NMR (CDCl$_3$, 300 MHz) δ: 1.01 (3H, t), 1.63 (3H, t), 1.85 (2H, m), 2.27 (3H, s), 2.50 (4H, t), 2.92 (2H, t), 3.10 (4H, t), 4.27 (3H, s), 4.37 (2H, q), 7.14 (1H, d), 7.83 (1H, dd), 8.83 (1H, d), 10.81 (1H, s); EI-MS m/z 474 (M$^+$, 4), 410 (8), 404 (58), 312 (7), 99 (100).

Method 2

In a 25 mL flask, the compound of formula (II) (1 g) from Preparation 4 was dissolved in water (5 mL). After the mixture was heated to reflux for 4 hours, dichloromethane (15 mL) was added to the solution, and the layers were separated. The organic phase was washed with brine (2×5 mL), dried over anhydrous sodium sulfate for 30 minutes, and distilled to remove the dichloromethane under reduced pressure to afford a white solid (0.80 g, yield 83%).

Method 3

In a 25 mL flash, the compound of formula (II) (1 g) from Preparation 4 was dissolved in 1 mol/L HCl aqueous solution (5 mL). After the reaction mixture was heated at 60° C. for 2 hours, the PH value of the mixture was adjusted to 8.5~9.5 with NaHCO$_3$ in an ice-water bath. The resulting white solid was collected by filtration and purified by re-crystallising with ethanol to a white powder (0.76 g, yield 79%).

Preparation 7

7-bromo-1-methyl-5-(2-ethoxyphenyl)-3-n-propyl-1,6-dihydro-7H-pyrazolo[4,3-d]pyrimidine (IV, X=Br)

Except for replacing POCl$_3$ with PBr$_3$, the title compound was prepared following the procedure of Method 2 in Preparation 3 (4.0 g, yield 67%).

Preparation 8

7-bromo-1-methyl-5-(2-ethoxy-5-chlorosulphonylphenyl)-3-n-propyl-1,6-dihydro-7H-pyrazolo[4,3-d]pyrimidine (III, X=Br)

Method 1

Except for replacing POCl$_3$ with PBr$_3$, the title compound was prepared following the procedure of Method 1 in Preparation 4 (5.0 g, yield 70%). $^1$H NMR (CDCl$_3$, 300 MHz) δ: 1.03 (3H, t), 1.43 (3H, t), 1.88 (2H, m), 3.04 (2H, t), 4.23 (2H, q), 4.40 (3H, s), 7.15 (1H, d), 8.07 (1H, dd), 8.45 (1H, d); EI-MS m/z 475 (8), 473 (M$^+$+1, 8), 382 (24), 380 (24), 292 (76), 82 (98), 80 (100), 79 (40).

Method 2

Except for replacing POCl$_3$ with PBr$_3$, the title compound was prepared following the procedure of Method 3 in Preparation 4 (3.4 g, yield 59%).

Method 3

Except for replacing POCl$_3$ with PBr$_3$, the title compound was prepared following the procedure of Method 6 in Preparation 4 (3.0 g, yield 52%).

Preparation 9

7-bromo-1-methyl-5-[2-ethoxy-5-(4-methylpiperazin-1-ylsulphonyl)phenyl]-3-n-propyl-1,6-dihydro-7H-pyrazolo[4,3-d]pyrimidine (II, X=Br)

The title compound was prepared from 7-bromo-1-methyl-5-(2-ethoxyphenyl-5-chlorophonyl)-3-n-propyl-1,6-dihydro-7H-pyrazolo[4,3-d]pyrimidine (III, X=Br) following the procedure of Method 1 in Preparation 5 (0.8 g, yield 72%). $^1$H NMR (CDCl$_3$, 300 MHz) δ: 1.03 (3H, t), 1.43 (3H, t), 1.87 (2H, m), 2.51 (3H, s), 2.83 (4H, s), 3.04 (2H, t), 3.50 (4H, s), 4.21 (2H, q), 4.39 (3H, s), 7.14 (1H, d), 7.77 (1H, dd), 8.20 (1H, s); EI-MS m/z 538 (M$^+$, 6), 536 (6), 468 (6), 466 (6), 456 (20), 99 (100).

Preparation 10

1-methyl-5-[2-ethoxy-5-(4-methylpiperazin 1-ylsulphonyl)phenyl]-3-n-propyl-1,6-dihydro-7H-pyrazolo[4,3-d]pyrimidin-7-one (1)

The title compound was prepared from 7-bromo-1-methyl-5-[2-ethoxy-5-(4-methylpiperazinylsulphonyl)phenyl]-3-n-propyl-1,6-dihydro-7H-pyrazolo[4,3-d]pyrimidine following the procedure of Method 1 in Preparation 6 (0.85 g, yield 75%).

Example 2 while X is Cl, a process for preparing the compound of formula (I) was as follows:

Step 1 The compound of formula (V) (5 g, 0.015 mol) was added into a 50 mL flask, and POCl$_3$ (10 mL) was added slowly to prepare a solution in an ice bath. After heated at 120° C. for 1 hour, the reaction mixture was poured into ice-water (30 mL) to quench the reaction, and then extracted with dichloromethane (3×30 mL). The combined organic phase was washed with brine (2×10 mL) and dried over anhydrous sodium sulfate for 30 minutes, followed by concentration in vacuo to obtain the compound of formula (IV) (4.1 g) as a white solid.

Step 2 The compound of formula (IV) (5 g, 0.015 mol) was added portionwise to chlorosulfonic acid (10 mL) in an ice bath, and the mixture was stirred in the ice bath for 30 minutes. After the ice bath was removed, the reaction continued for another 2 hours, and then the residue was poured into water. The resulting white solid was collected by filtration, washed with ice-water until the dropwise filtrate was neutral, and dried under vacuum to obtain the compound of formula (III) as a white solid.

Step 3 The compound of formula (III) (2 g) was dissolved in dichloromethane (20 mL) and triethylamine (0.94 g, 9.3 mmol) to prepare a solution. A solution of 1-methylpiperazine (0.51 g, 5.1 mmol) in dichloromethane (5 mL) was then added dropwise to the solution in an ice bath. After the ice bath was removed, the mixture was stirred at room temperature for 2 hours. Water was added, and the layers were separated. The organic phase was washed with saturated aqueous ammonium chloride solution (2×10 ml) and brine (2×10 mL), dried over anhydrous Na$_2$SO$_4$ (1 g) for 30 minutes, and distilled under reduced pressure to remove the solvent to afford crude of formula (II) as a white solid, which was then purified by re-crystallising with dichloromethane/petroleum ether to obtain the compound of formula (II) as a white crystal.

Step 4 The compound of formula (II) (1 g) was dissolved in tert-butyl alcohol (3 mL) and an appropriate amount of water to prepare a solution, followed by addition of NaHCO$_3$ (2.1 mmol). After the mixture was heated at 90° C. for 1.5 hours, the tert-butyl alcohol was removed by distillation under reduced pressure at 40° C. The PH value of solution was adjusted to 8.5~9.5, and the resulting white solid was collected by filtration and purified by re-crystallising with ethanol to obtain the compound of formula (I) (0.87 g) as a white needle crystal.

Alternative A: Step 1 could be followed immediately by Step 2 without purifying the intermediate, and the detailed procedure was as follow:

The compound of formula (V) (5 g, 0.015 mol) was added into a 50 mL three-neck flask, and POCl$_3$ (10 mL) was added slowly to prepare a solution in an ice bath. After heated at 120° C. for 1 hour, the reaction mixture was cooled to a temperature below 0° C., followed by addition of chlorosulfonic acid (10 mL). 30 minutes later, the ice bath was removed, and the reaction mixture was stirred at the room temperature for 2 hours. The mixture was poured into ice-water (30 mL), the resulting white solid was collected by filtration, washed with ice-water until the dropwise filtrate was neutral, and dried under vacuum for 3 hours at 35° C. to obtain the compound of formula III (5.7 g) as a white solid.

The processes for the preparation of the intermediates in the present invention were as follows.

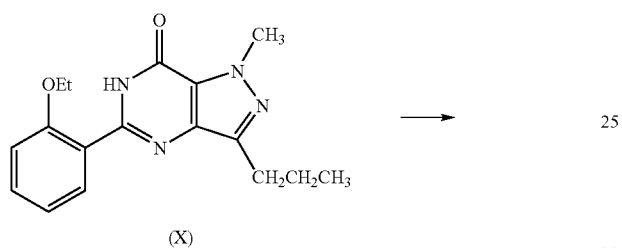

(X)

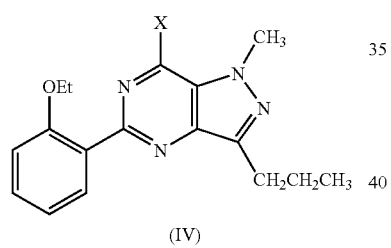

(IV)

The compound of formula (X) (5 g, 0.016 mol) was added into a 50 mL three-neck flask in an ice bath, followed by dropwise addition of POCl$_3$ (10 mL). After heated for 4 hours at 50° C., the reaction mixture was poured into ice to quench the reaction, and extracted with dichloromethane (3×30 mL). The combined organic phase was washed with brine (2×10 mL) and dried over anhydrous sodium sulfate (2 g) for 30 minutes, followed by concentration in vacuo to give the compound of formula (IV) (4.4 g).

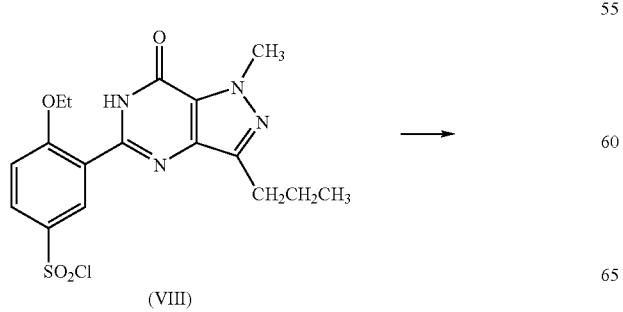

(VIII)

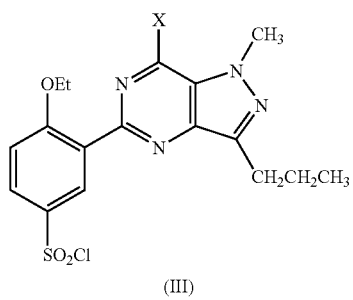

(III)

The compound of formula (VIII) (5 g, 0.012 mol) was added into a 50 mL flask, and POCl$_3$ (10 mL) was added slowly to prepare a solution. The reaction mixture was heated at 60° C. for 3 hours and then poured into water (20 mL). The resulting white solid was collected by filtration, washed with ice-water until the dropwise filtrate was neutral, and dried under vacuum for 2 hours at 35° C. to obtain the compound of formula (III) (4.8 g).

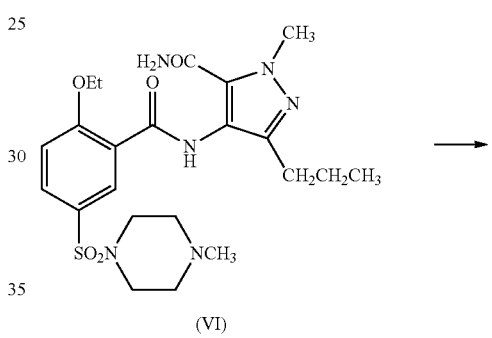

(VI)

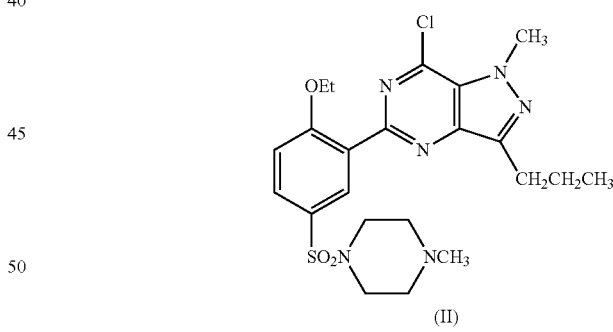

(II)

The compound of formula (VI) (2 g, 0.004 mol) was added into a 50 mL flask, and POCl$_3$ (10 mL) was added slowly to prepare a solution. The reaction mixture was heated at 100° C. for 1.5 hours and then poured onto crush ice. The resulting white solid was collected by filtration, washed with ice-water until the dropwise filtrate was neutral, and dried under vacuum for 2 hours at 35° C. to obtain the compound of formula (II) (1.5 g).

While X is Br, the processes for preparing some intermediates in the present invention were as follows.

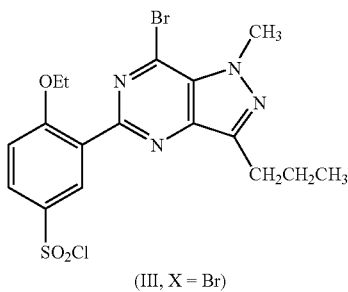

(III, X = Br)

The compound of formula (III, X=Br) was prepared by replacing $POCl_3$ with $PBr_3$ following the procedure of Alternative A (5.0 g).

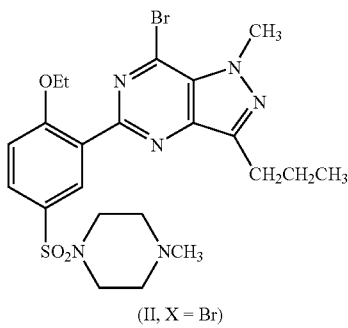

(II, X = Br)

The compound of formula (II, X=Br) was prepared from the compound of formula (III, X=Br, 1.0 g) following the procedure of Step 3 (0.8 g).

The compound of formula I was prepared from the compound of formula (II, X=Br, 0.5 g) following the procedure of Step 4 (0.36 g).

The process of the present invention reduces side reactions in the previous processes, e.g. the isomerization of pyrimidine skeleton and cleavage of the 5-ethoxy group on benzene ring in base-catalyzed cyclization. These improvements lead to higher yields with more convenient operation, resulting in a better industrial applicability.

We claim:

1. A compound of formula (II)

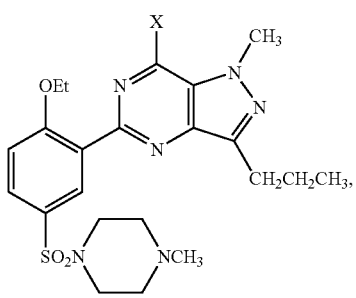

(II)

Wherein X is Cl or Br.

2. A process for the preparation of the compound of formula (II) according to claim 1, comprising one step of:
   treating the compound of formula (III) with methylpiperazine, as illustrated in the following scheme:

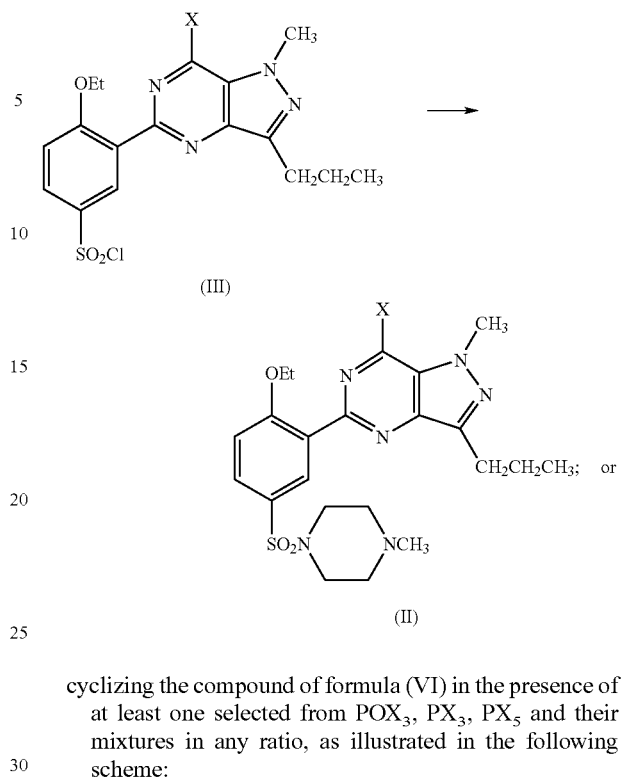

cyclizing the compound of formula (VI) in the presence of at least one selected from $POX_3$, $PX_3$, $PX_5$ and their mixtures in any ratio, as illustrated in the following scheme:

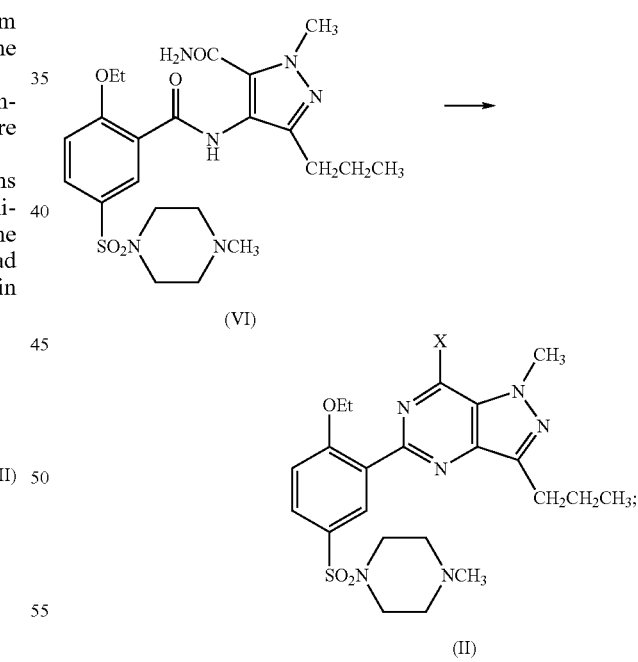

Wherein X is Cl or Br.

3. A process for the preparation of the compound of formula (II) according to claim 2, comprising one step of:
   treating the compound of formula (III) in a solvent selected from a group consisting of alkyl halides, lower fatty ketones and other ethers, followed by adding a base and methylpiperazine and collecting the desired compound from reaction mixtures; or heating the compound of formula (VI) in the presence of at least one selected from POX$_3$, PX$_3$, PX$_5$ and their mixtures in any ratio at 50~120° C., followed by pouring the reaction mixture into water, ice or their mixtures and collecting the desired precipitate, wherein the cyclization is carried out in the presence of a solvent selected from a group consisting of benzene, toluene, CH$_2$Cl$_2$, CHCl$_3$, ClCH$_2$CH$_2$Cl, THF, dioxane and their mixtures in any ratio.

4. A process for the preparation of the compound of formula (I), wherein the compound of formula (I) is prepared from the compound of formula (II), as illustrated in the following scheme:

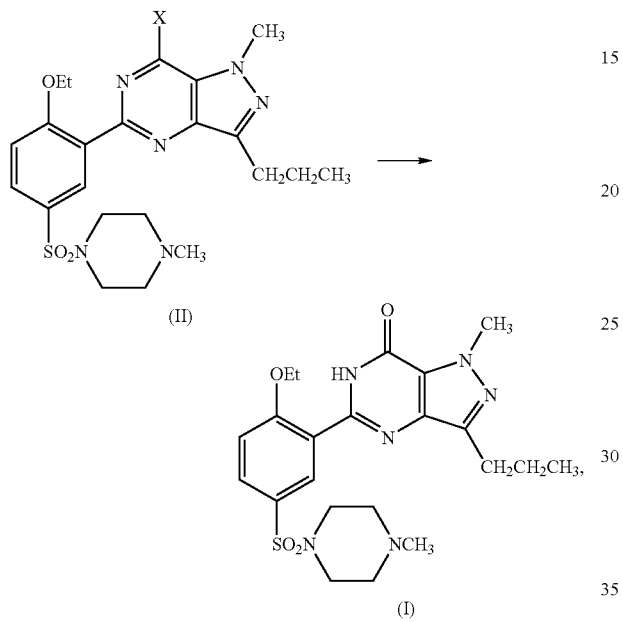

Wherein X is Cl or Br.

5. A process for the preparation of the compound of formula (I) according to claim 4, wherein the reaction is carried out in a solvent selected from a group consisting of water, methanol, ethanol, isopropanol, t-C$_4$H$_9$OH, glycol, ethylene glycol monomethyl ether and mixtures thereof; or optionally further adding a base selected from a group consisting of alkali metal alkoxides, alkali metal hydrides, alkaline earth metal hydrides, amines, amine metal derivatives, hydroxides, carbonates, bicarbonates and their mixtures in any ratio; or further adding acid selected from a group consisting of hydrochloric acid, sulfuric acid, phosphoric acid, citric acid, tartaric acid, maleic acid and mixtures thereof.

6. A process for the preparation of the compound of formula (I) according to claim 4, comprising one step of: treating the compound of formula (III) with methylpiperazine, as illustrated in the following scheme:

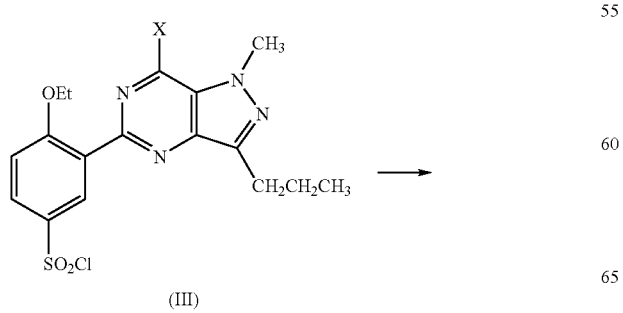

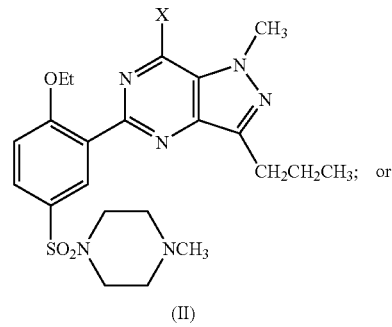

cyclizing the compound of formula (VI) in the presence of at least one selected from POX$_3$, PX$_3$, PX$_5$ and their mixtures in any ratio, as illustrated in the following scheme:

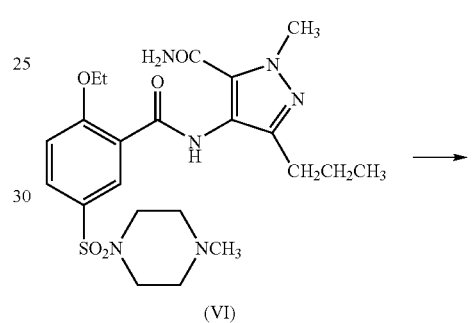

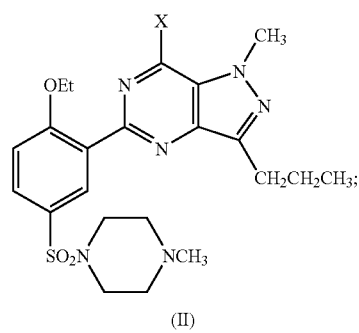

Wherein X is Cl or Br.

7. A process for the preparation of the compound of formula (II) according to claim 4, comprising one step of:

treating the compound of formula (III) in a solvent selected from a group consisting of alkyl halides, lower fatty ketones and other ethers, followed by adding a base and methylpiperazine and collecting the desired compound from reaction mixtures; or heating the compound of formula (VI) in the presence of at least one selected from POX$_3$, PX$_3$, PX$_5$ and their mixtures in any ratio at 50~120° C., followed by pouring the reaction mixture into water, ice or their mixtures and collecting the desired precipitate, wherein the cyclization is carried out in the presence of a solvent selected from a group consisting of benzene, toluene, CH$_2$Cl$_2$, CHCl$_3$, ClCH$_2$CH$_2$Cl, THF, dioxane and their mixtures in any ratio.

8. A process for the preparation of the compound of formula (II) according to claim 5, comprising one step of:
treating the compound of formula (III) with methylpiperazine, as illustrated in the following scheme:

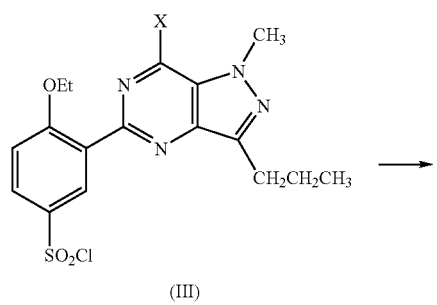

(III)

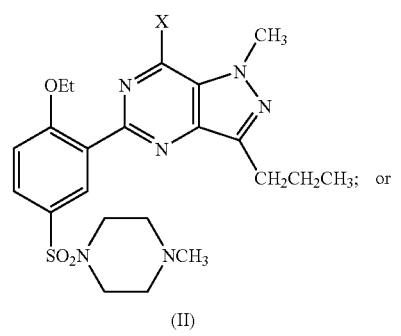

(II)

cyclizing the compound of formula (VI) in the presence of at least one selected from $POX_3$, $PX_3$, $PX_5$ and their mixtures in any ratio, as illustrated in the following scheme:

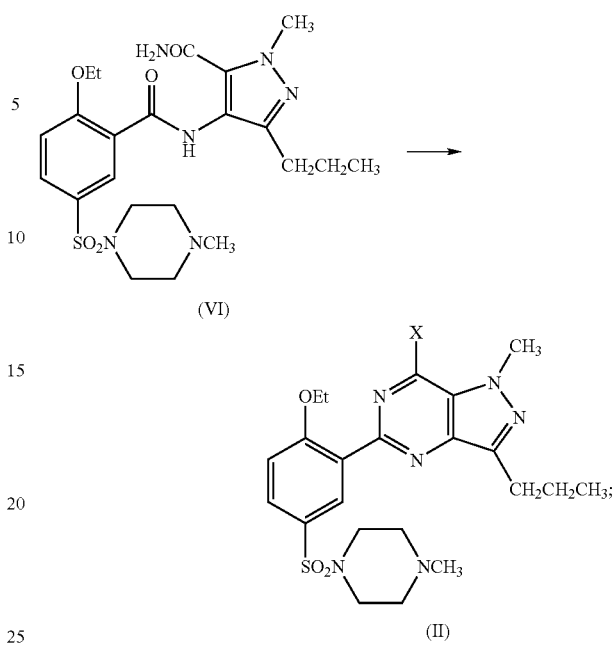

Wherein X is Cl or Br.

9. A process for the preparation of the compound of formula (II) according to claim 5, comprising one step of:
treating the compound of formula (III) in a solvent selected from a group consisting of alkyl halides, lower fatty ketones and other ethers, followed by adding a base and methylpiperazine and collecting the desired compound from reaction mixtures; or heating the compound of formula (VI) in the presence of at least one selected from $POX_3$, $PX_3$, $PX_5$ and their mixtures in any ratio at 50~120° C., followed by pouring the reaction mixture into water, ice or their mixtures and collecting the desired precipitate, wherein the cyclization is carried out in the presence of a solvent selected from a group consisting of benzene, toluene, $CH_2Cl_2$, $CHCl_3$, $ClCH_2CH_2Cl$, THF, dioxane and their mixtures in any ratio.

* * * * *